United States Patent
Zhang et al.

(10) Patent No.: US 6,301,878 B1
(45) Date of Patent: Oct. 16, 2001

(54) METHOD AND APPARATUS FOR EXHAUST GAS CLEANING WITH TRIM CONTROL

(75) Inventors: Hong Zhang; Corinna Pfleger, both of Regensburg; Juergen Roessler, Muennerstadt, all of (DE)

(73) Assignee: Siemens Aktiengesellschaft (DE)

( * ) Notice: Subject to any disclaimer, the term of this patent is extended or adjusted under 35 U.S.C. 154(b) by 0 days.

(21) Appl. No.: 09/437,217

(22) Filed: Nov. 10, 1999

(30) Foreign Application Priority Data

Nov. 12, 1998 (DE) .............................. 198 52 244

(51) Int. Cl.$^7$ ....................................... F01N 3/00
(52) U.S. Cl. ................ 60/274; 60/275; 60/276; 60/277; 204/425
(58) Field of Search ............................ 60/274, 276, 277, 60/275, 297; 204/425, 426, 427

(56) References Cited

U.S. PATENT DOCUMENTS

| | | | |
|---|---|---|---|
| 4,107,019 | * 8/1978 | Takao et al. | 204/195 S |
| 4,384,935 | * 5/1983 | De Jong | 204/406 |
| 5,540,047 | * 7/1996 | Dahlheim et al. | 60/274 |
| 5,782,087 | * 7/1998 | Kinugasa et al. | 60/276 |
| 5,974,793 | * 11/1999 | Kinugasa et al. | 60/285 |
| 6,047,542 | * 4/2000 | Kinugasa et al. | 60/274 |
| 6,069,013 | * 5/2000 | Plog et al. | 436/113 |
| 6,076,393 | * 6/2000 | Kato et al. | 73/31.05 |

FOREIGN PATENT DOCUMENTS

| | | |
|---|---|---|
| 195 43 219 C1 | 11/1995 | (DE) . |
| 0 814 249 A2 | 12/1997 | (EP) . |

OTHER PUBLICATIONS

Kato, et al, *Performance of Thick Film Nox Sensor on Diesel and Gasoline Engines*, SAE Paper 970858, 1997.

* cited by examiner

Primary Examiner—Thomas Denion
Assistant Examiner—Binh Tran

(57) ABSTRACT

The present invention includes a method and apparatus for cleaning exhaust of an internal combustion engine. The internal combustion engine has a catalyst and a lambda probe disposed in an exhaust gas tract. The lambda probe is disposed upstream from the catalyst, and is capable of an output $\lambda o$ substantially close to lambda=1. The present invention includes determining a relationship between a downstream NOx concentration and a lambda value such that a lambda value substantially greater than 1 indicates a substantially greatly increased NOx concentration, and determining a relationship between a downstream $NH_3$ concentration and a lambda value such that a lambda value substantially less than 1 indicates a substantially greatly increased $NH_3$ concentration.

16 Claims, 3 Drawing Sheets

METHOD AND APPARATUS FOR EXHAUST GAS CLEANING WITH TRIM CONTROL

REFERENCE TO PRIORITY APPLICATION

This application claims the benefit of priority to German Application No. 198 52 244.4, filed Nov. 12, 1998, which is hereby incorporated by reference in its entirety.

BACKGROUND OF THE INVENTION

The present invention relates to a method and apparatus for cleaning the exhaust gas of an internal combustion engine, and more specifically to a method and apparatus which uses an NOx pickup to determine the amount of oxygen present in an exhaust gas by measuring the decomposition of $NH_3$ in the NOx pickup.

It is known to use a three-way catalyst in the exhaust gas tract of an internal combustion engine to clean the exhaust gas. It is also known to use provide a lambda probe whose output signal is dependent upon the residual oxygen content in the raw exhaust upstream from the catalyst. It is believed that the residual oxygen content in the raw exhaust depends upon the fuel/air mixture dispersed in the internal combustion engine. It is known that in case of excess fuel (rich mixture), the residual oxygen content in the raw exhaust is lower, and in case of excess air (lean mixture), the residual oxygen content in the raw exhaust is higher.

It is known that in a lean mixture (lambda>1), an output voltage of the lambda probe is usually less than about 100 mV. It is also known that the output voltage of the lambda probe changes almost abruptly near lambda=1, and the output voltage of the lambda probe increase to about 0.8 volt in rich mixture (lambda<1). This is referred to as a two-point action.

There are also known broad-band lambda probes that are capable of outputting signals corresponding to a lambda range (0.7 to 4) in a linear fashion.

It is known to operate an internal combustion engine such that the signal output by the lambda probe, indicating the residual oxygen level in the raw exhaust, varies around a predetermined average which corresponds to a value for lambda=1, for example. It is believed that a three-way catalyst has a certain lambda value λo with optimal catalytic properties. Thus, the predetermined average of lambda values during the operation of the internal combustion engine should actually be substantially λo. It is also known, however, to vary the lambda value λo for optimum catalytic properties from lambda=1, for example lambda=0.99.

It is believed that static and dynamic properties of the lambda probe upstream from the three-way catalyst are altered by aging and poisoning. It is believed that this causes a position of a signal level corresponding to λo to change. It is known to use an additional lambda probe downstream from the three-way catalyst, which is believed to be less sensitive to poisoning. It is believed that the additional lambda probe may serve as a monitor probe to measure and confirm the catalytic conversion and permit fine regulation of the fuel/air mixture by correcting the signal level corresponding to λo in the lambda probe upstream, such that the lambda value λo most favorable to catalytic conversion is maintained. This process is called "guiding control" or "trimming."

It is believed that in order further to reduce pollutant emissions from internal combustion engines, an NOx catalyst can be provided in addition to the three-way catalyst. It is known that the NOx catalyst can also be integrated into the three-way catalyst. It is also known to use a storage catalyst that includes one state of operation which stores NOx and another state of operation which converts the stored NOx. It is known to use a measuring pickup sensitive to NOx downstream from the NOx catalyst to achieve the optimum operation of an NOx catalyst.

The present invention addresses the problem of substantially effectively reducing a residual oxygen content of an exhaust gas of an internal combustion engine without the use of an additional lambda probe downstream of a catalytic converter.

SUMMARY OF THE INVENTION

The present invention provides a method for cleaning the exhaust gas of an internal combustion engine with a catalyst having three-way properties disposed in the exhaust tract and a lambda probe disposed upstream from the catalyst, in which the control of the operation of the internal combustion engine is performed such that the lambda value of the raw exhaust gas assumes predetermined values at the lambda probe, while a certain signal level of the lambda probe is associated with a lambda value λo which is close to lambda=1, the concentration of an exhaust gas component downstream from the catalyst showing three-way properties is measured by means of an additional measuring pickup, and the signal level associated with the λo is corrected accordingly, characterized in that an NOx measuring pickup is used as an additional measuring pickup which detects the NOx concentration in the exhaust gas, a relationship between NOx concentration in the exhaust gas and the lambda value of the exhaust gas is given such that for lambda values>1 the NOx concentration increases greatly and with it the output signal of the measuring pickup, which shows a cross-sensitivity to $NH_3$, so that for lambda values <1 the output signal of the measuring pickup likewise increases, and which has an internal signal which at lambda=1 has a sign change, and a correction of the signal level associated with λo is performed using the relationship between the NOx concentration in the exhaust gas and the lambda value of the exhaust gas by means of the output signal and the internal signal of the measuring pickup.

The present invention also provides an apparatus for cleaning the exhaust gas of an internal combustion engine having a catalyst disposed in the exhaust tract and having three-way properties, a lambda probe disposed upstream from the catalyst, an operation control apparatus which controls the operation of the internal combustion engine such that the exhaust gas at the lambda probe assumes predetermined lambda values, while a certain signal level of the lambda probe is associated with a lambda value λo which is close to lambda=1, and an additional measuring pickup disposed downstream of the catalyst, which detects the concentration of an exhaust gas component, characterized in that the additional measuring pickup is an NOx measuring pickup which detects the NOx concentration in the exhaust gas, a relationship between NOx concentration in the exhaust gas and the lambda value of the exhaust gas is given such that, for lambda values>1 the NOx concentration in the exhaust gas and thus the output signal of the measuring pickup increases greatly, which shows a cross-sensitivity to $NH_3$ so that for lambda values<1 the output signal of the measuring pickup likewise increases, which has an internal signal (Ip0) which has a sign change at lambda=1, and which is so connected with the operation control apparatus such that the output signal and the internal signal (Ip0) are fed to it so that the operation control apparatus, utilizing the relationship between the NOx concentration in the exhaust gas and the lambda value of the exhaust gas, performs a correction of the signal level associated with λo by means of the output signal and of the internal signal (Ip0) of the measuring pickup.

According to the present invention, a measuring pickup is provided downstream from the catalyst having three-way properties, and it detects the NOx concentration in the exhaust gas. Between the NOx concentration and the lambda value there is a relationship which is utilized for correcting the signal level, associated with λo, of the probe situated upstream from the catalyst.

The invention sets out from the knowledge that the signal of the measurement pickup has only a local minimum near the λo-associated value at the NOx concentration corresponding to lambda=1, if the measuring pickup detecting the NOx concentration shows a cross sensitivity to $NH_3$. This is the case, for example, with known oxygen ion-conducting solid electrolyte measuring pickups which have a measuring cell in which an oxygen concentration corresponding to lambda=1 is established. Thus, such a measurement of the association does not permit a clear association of an NOx concentration with a lambda value, and especially no clear association of the lambda value λo close to lambda=1 with a value of the output signal of the measuring pickup.

According to the invention, therefore, an internal signal of the measuring pickup is additionally utilized for a trimming adjustment and it shows a change in sign at lambda=1. With the aid of the sign of this internal signal the output signal giving the NOx concentration can be definitely associated with a lambda value, since the lambda<1 range can be distinguished from lambda>1, although the output signal of the measuring pickup alone does not permit this distinction, since it has only a local minimum at lambda=1.

Thus, without the use of a separate lambda probe arranged downstream from the catalyst, a trimming adjustment can be performed and it can be assured that the catalyst is operating in the range of optimum lambda values, i.e., at λo with a maximum conversion rate.

In comparison with the use of a separate lambda probe downstream from the catalyst for trimming adjustment, the result is an improved accuracy of the trimming adjustment due to the great steepness of the NOx concentration in the lambda>1 range and the steepness of the characteristic imposed by the $NH_3$ cross-sensitivity, in conjunction with the utilization of the internal signal. In comparison with the Applicant's prior German patent application DE 198 19 461.7 A1, the result is furthermore the advantage that it is easier to detect any drifting of the mixture in the internal combustion engine toward richness and thus to values of lambda<1 in the exhaust lambda value. This is brought about by the fact that the cross-sensitivity of the measuring pickup to the $NH_3$ in the rich exhaust gas is deliberately exploited and the internal signal is used in addition to the output signal of the measuring pickup indicating the NOx concentration.

Advantageously, a thick-film measuring pickup is used as the NOx measuring pickup. Such a measuring pickup is described in the publication of N. Kato et al., "Performance of Thick Film NOx Probe on Diesel and Gasoline Engines," Society of Automotive Engineers, publication 970858, 1997. This measuring pickup has two measuring cells and consists of a zirconium oxide that conducts oxygen ions. It embodies the following concept: In a first measuring cell, to which the gas being measured is fed through a diffusion barrier, a first oxygen ion pumped current is used to establish a first oxygen concentration, at which no decomposition of NOx takes place. In a second measuring cell, which is connected through a diffusion barrier to the first measuring cell, the oxygen content is further lowered by means of a second oxygen ion pumped current and NOx is decomposed at a measuring electrode. The oxygen thus produced is determined as a measure of the NOx concentration.

In a measuring pickup of this kind the first oxygen ion pumping current can be brought out as the internal signal.

The use of an NOx measuring pickup for the trimming adjustment is advantageous especially when such a pickup is present anyway for controlling an NOx catalyst.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention.

DETAILED DESCRIPTION OF THE PREFERRED EMBODIMENTS

Figure 1:
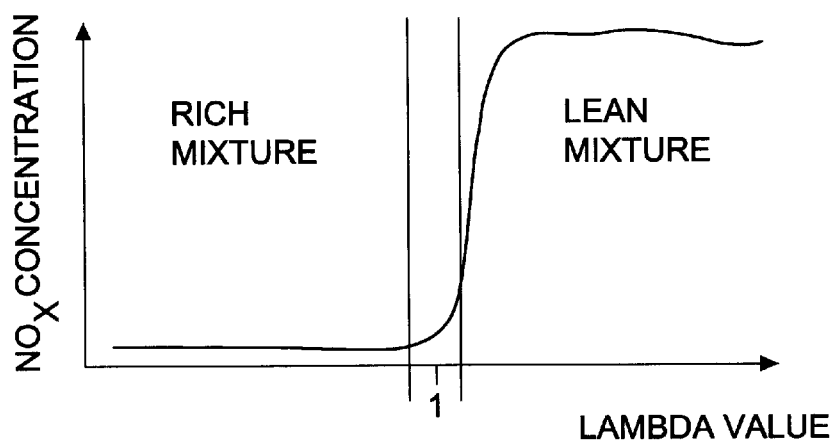
FIG. 1 is a diagram showing the relationship between the lambda value and the NOx concentration in the exhaust of an internal combustion engine downstream from a three-way catalyst.
Figure 2:
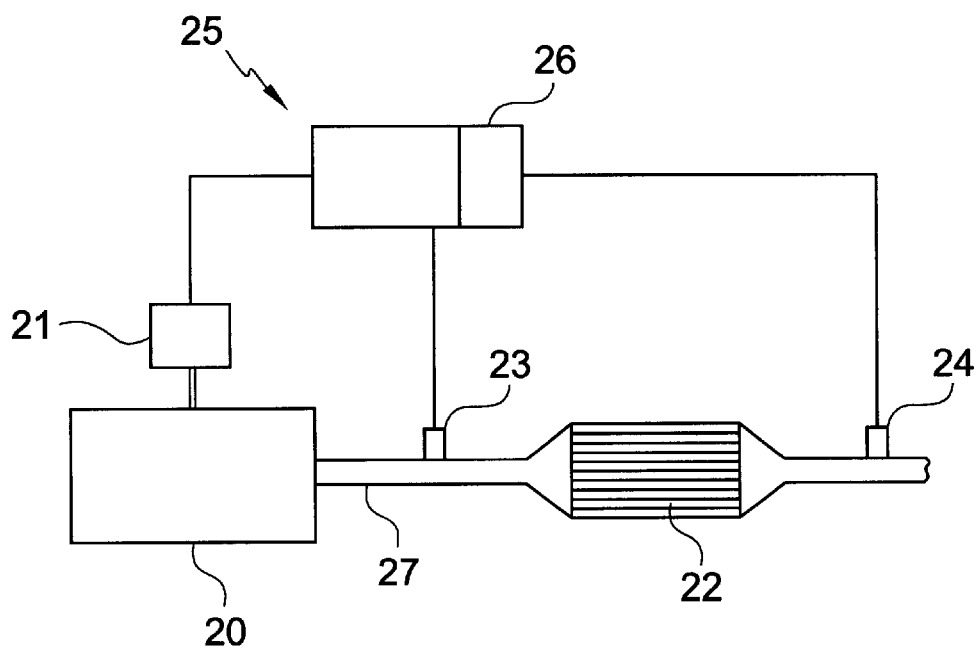
FIG. 2 is a block diagram of an internal combustion engine with an exhaust cleaning system.

FIG. 1 is a diagram showing the relationship between the lambda value and the NOx concentration in the exhaust of an internal combustion engine downstream from a three-way catalyst. FIG. 2 is a block diagram of an internal combustion engine with an exhaust cleaning system. The lambda value of an exhaust of an internal combustion engine 20 corresponds to an NOx concentration in the exhaust when the NOx is not being stored in an exhaust gas tract 27. The internal combustion engine 20 can be an air induction or a direct injection engine. The operation of the internal combustion engine 20 is controlled by an operation control apparatus 25. A fuel feeding system 21, which can be in the form of an injection system, is controlled by the operation control apparatus 25 through lines not shown in the drawing, and provides for the dispersement of fuel to the internal combustion engine 20. The exhaust gas tract 27 is attached to an engine exhaust portion. The exhaust gas tract 27 includes a three-way catalyst 22 having an NOx reducing function and an NOx measuring pickup 24. Separate catalysts can also be used, for example, an NOx storage catalyst and a three-way catalyst. The three-way catalyst 22 has a lambda value λo with optimal catalytic properties. Depending on the catalyst, λo can be between 0.99 and 1.

A broad-band lambda probe 23 is provided upstream of the three-way catalyst 22. The broad-band lambda probe outputs measurement, through lines not represented, to the operation control apparatus 25. By this arrangement, the broad-band lambda probe 23 is able to vary the operating characteristics of the internal combustion engine 20. In addition, the operational characteristics of the internal combustion engine 20 will be varied and determined by additional probes and pickups which output information to the operation control apparatus 25 including rotatory speed, load, catalyst temperature etc.

The operation of the internal combustion engine 20 is performed in one type of operation where an average predetermined output signal level from the broad-band lambda probe 23 corresponds to a residual oxygen content in a raw exhaust. In the case of a normal, fully operational broad-band lambda probe 23, this output signal level corresponds to λo, i.e., to the lambda value at which the catalyst 22 shows optimal catalytic properties.

In FIG. 1, lambda values are shown on the x-axis, and NOx concentrations are shown on the y-axis. As shown, NOx concentrations increase at a substantially high rate for lean mixtures (lambda>1), and NOx concentrations assume substantially low values for rich mixtures (lambda<1). A catalyst window having substantially optimal catalytic properties is represented by two vertical broken lines in FIG. 1. On account of the flat curve of the NOx concentration in the area of the catalyst window, which is represented by two vertical broken lines in FIG. 1, evaluation of the signal from the pickup 24 indicating NOx concentration for lambda values<1 is not possible or very difficult. As a rule only a one-sided control is able reliably to prevent the lambda value from drifting toward a rich mixture (lambda<1).

Most NOx measuring pickups, however, have a cross-sensitivity to $NH_3$. This is especially true of thick film solid electrolyte pickups using Nernst measuring cells. A measuring pickup of this kind is used as the pickup 24.

Figure 4:
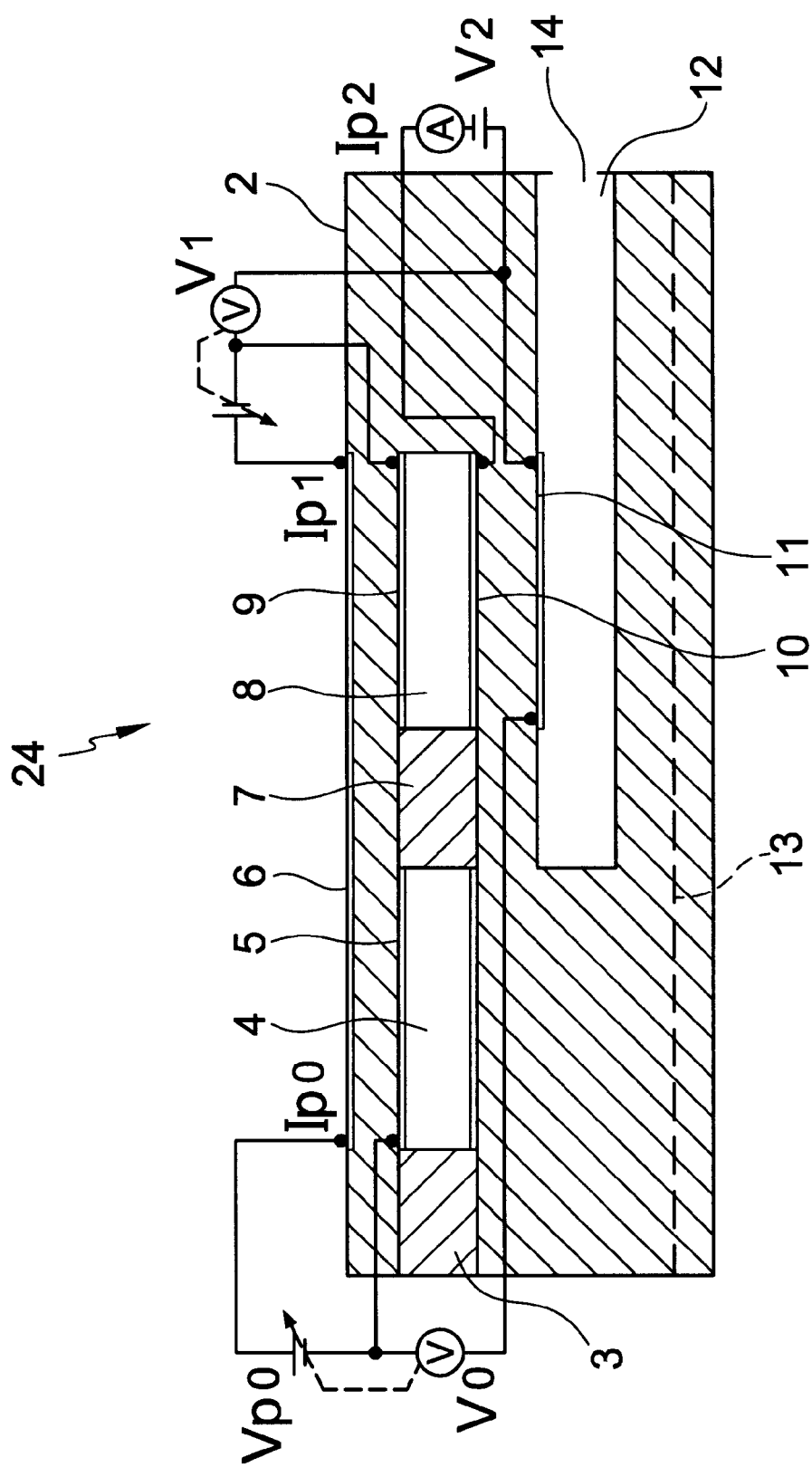
FIG. 4 is a schematic sectional representation of a measuring pickup detecting the NOx concentration.

FIG. 4 is a schematic sectional representation of a measuring pickup detecting the NOx concentration. It is used in the apparatus represented in FIG. 2 as a pickup 24 for measuring the NOx concentration in the exhaust gas tract 27 of the internal combustion engine 20. The pickup 24 consists of a solid electrolyte 2 which is enveloped by the gas being measured and is heated by a heater 13. The exhaust gas diffuses through a diffusion barrier 3 into a first cell 4. The oxygen content in this cell 4 is measured by a first Nernst voltage V0 between a first electrode 5 and a reference electrode 11 exposed to the ambient air. The reference electrode 11 is disposed in an air duct 12 into which ambient air passes through an opening 14. Both electrodes are conventional platinum electrodes. The value measured for the first Nernst voltage V0 is used for the purpose of establishing a set voltage Vp0. The set voltage Vp0 drives a first oxygen ion pump current Ip0 through the solid electrolyte 2 between the first electrode 5 and an external electrode 6. The consequence of the controlling intervention, represented by a broken line, of the first Nernst voltage V0 into the set voltage Vp0 is that in the first measuring cell 4 a predetermined initial oxygen concentration is present.

The first measuring cell 4 is connected to a second measuring cell 8 through an additional diffusion barrier 7. The gas present in the cell 4 diffuses through this diffusion barrier 7. The second oxygen concentration in the additional cell 8 is measured by a second Nernst voltage V1 between a second electrode 9, which is likewise a platinum electrode, and the reference electrode 11 and used to control a second oxygen ion pumping current Ip1. The second oxygen ion pumping current Ip1 from the first measuring cell 4 runs from the second electrode 9 through the solid electrolyte 2 to the external electrode 6. By means of the second Nernst voltage V1 it is regulated such that, in the second cell 8, a predetermined small, second oxygen concentration is present. The NOx that is not affected by the previous procedures in measuring cells 4 and 8 is now decomposed at the measuring electrode 10, which is given a catalytic action, by applying the voltage V2 between the measuring electrode 10 and the reference electrode 11, and the liberated oxygen is pumped through the solid electrolyte 2 in a third oxygen ion pumping current Ip2 to the reference electrode 11. This third oxygen ion pumping current Ip2, if the residual oxygen content at the measuring electrode 10 is sufficiently low, is carried only by oxygen ions which originate in the decomposition of NOx. The current Ip2 is thus a measure of the NOx concentration in the measuring cell 8 and thus in the exhaust gas being measured and constitutes the output signal of the measuring pickup 24.

In this NOx measuring pickup 24, however, which is cross-sensitive to $NH_3$, the conversion of $NH_3$ to NOx takes place in the first measuring cell 4, $O_2$ being consumed out of the measuring cell. Thus, on account of this lowering of the oxygen content, the first Nernst voltage V0 turns out to be greater than corresponds to the oxygen content and thus to the lambda value in the exhaust gas. Accordingly the amount of the pumping current Ip0 is increased whenever $NH_3$ is present in the exhaust gas. Since $NH_3$ is present in the exhaust gas mainly in a rich mixture, the measuring pickup 24 shows, due to this cross-sensitivity to $NH_3$, an output signal for lambda values<1 which is greater than that of a non-cross-sensitive measuring pickup. The resultant characteristic curve is represented in FIG. 5.

Figure 5:
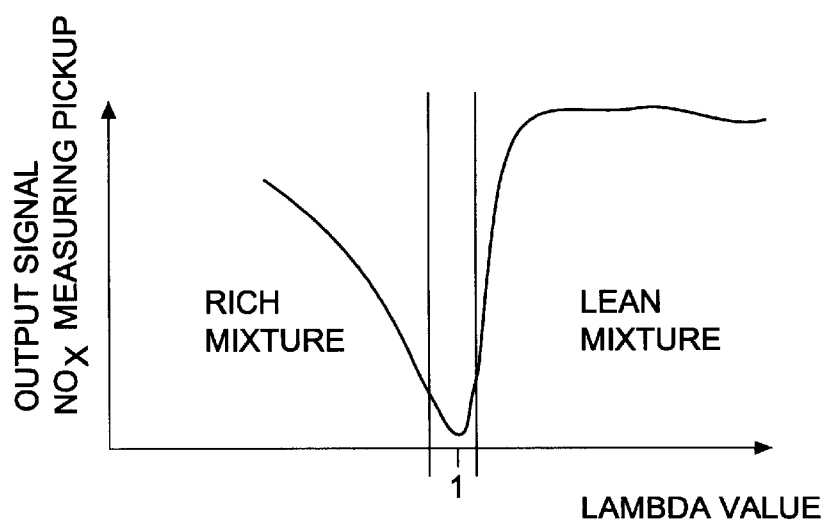
FIG. 5 is a diagram similar to that of FIG. 1 for the measuring pickup of FIG. 4, showing a cross-sensitivity to $NH_3$.

As shown, the curve of FIG. 5 has a minimum at lambda=1. It rises toward rich mixture due to the $NH_3$ cross-sensitivity. It rises toward lean mixture due to the abruptly rising NOx concentration in the lean mixture.

Since the oxygen concentration is measured in the first measuring cell 4 through the Nernst voltage V0 and is adjusted by means of the oxygen ion pumping current Ip0 or its set voltage Vp0 to a predetermined first oxygen concentration which corresponds to lambda=1 in the exhaust gas, the sign of Ip0 changes at lambda=1 for the following reasons: If the exhaust gas has a lambda value<1, the set voltage Vp0 produces an oxygen ion pumping current Ip0 on the basis that the first oxygen concentration in the first measuring cell 4 corresponds to lambda=1; so an oxygen ion pumping current flows from the reference electrode 11 located in the air duct 12 into the first measuring cell 4 to the first electrode 5. If, on the other hand, the lambda value of the exhaust gas is over 1, the set voltage Vp0 produces an oxygen ion pumping current Ip0 in the opposite direction, i.e., with a different sign. The first oxygen ion pumping current Ip0 therefore changes its sign when lambda=1.

The trimming adjustment is thus achieved as follows: The NOx measuring pickup 24 detects the NOx concentration in the exhaust gas downstream from the catalyst 22. The output signal as well as the oxygen ion pumping current Ip0 is carried to a trimming adjuster 26 which can be a self-contained device or can be provided in the operation control apparatus 25. To make fine adjustments of the signal level of the lambda probe 23 associated with the λo, and compensate changes of the lambda probe 23, the mixture of the internal combustion engine is adjusted to a special value of the NOx concentration. Since the signal put out by the measuring pickup 24 at lambda=1, however, has only a local minimum, the first oxygen ion pumping current Ip0 of measuring pickup 24 must be evaluated in order to decide whether an output signal from the NOx measuring pickup 24 is to be associated with the lambda<1 range or with the lambda>1 range. The sign of this internal signal shows this unmistakably. The evaluation is made easier or possible since the amount of the pumping current Ip0 is increased in the case of a rich mixture due to the $NH_3$ cross-sensitivity, so that noise components of the pumping current Ip0 become negligible.

The trimming adjuster 26 then recognizes a shift of the signal level of the lambda probe 23 that is caused, for example, by aging, and compensates for it, so as to assure that the internal combustion engine 20 is regulated by the operation control apparatus 25 such that the average lambda value of the raw exhaust gas in the exhaust tract 27 upstream of the catalyst 22 corresponds to the desired $\lambda o$ value.

Figure 3:
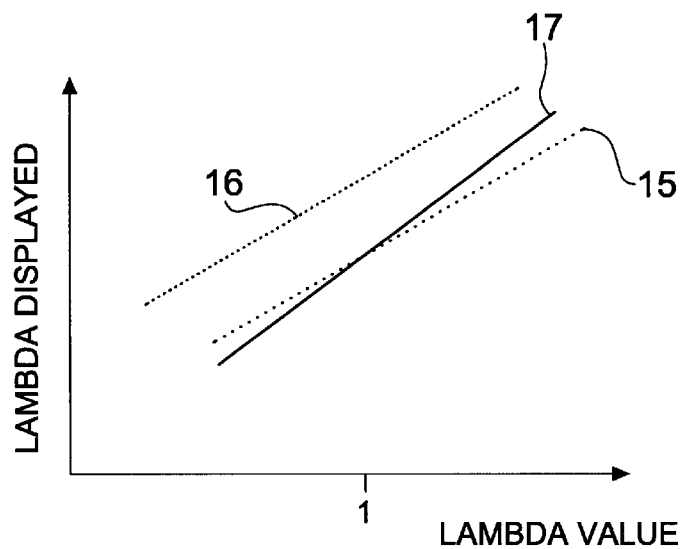
FIG. 3 is a diagram which shows the indicated lambda value for various broad-band lambda probes in relation to the actual lambda value.

In FIG. 3 the action of the trimming adjustment on the signal curve of the broad band lambda probe 23 is represented. The solid line 17 corresponds to an ideal probe, in which the displayed lambda value always is the same as the actual lambda value. An aged lambda probe shows, for example, the narrower broken curve 16. This lambda probe shows lambda values that are too high and it shows also a reduced sensitivity. The curve 16 can be corrected by the trimming adjustment such that the signal of the aged lambda probe 23 comes close to that of a probe with curve 16 which approaches very closely, around $\lambda o$ and lambda=1, to the ideal curve 17. Curve 15 represents a curve 16 which is corrected to approach very closely the solid line 17 of an ideal probe.

While in the state of the art a lambda probe would be necessary downstream from the catalyst 22 in order to detect the lambda value in the treated exhaust gas after the catalyst 22, and thereby adjust the mixture such that the raw exhaust gas will be close to the value $\lambda o$, this lambda probe can be dispensed with, according to the invention, and the NOx measuring pickup 24 can be used instead.

While the invention has been disclosed with reference to certain preferred embodiments, numerous modifications, alterations, and changes to the described embodiments are possible without departing from the sphere and scope of the invention, as defined in the appended claims and their equivalents thereof. Accordingly, it is intended that the invention not be limited to the described embodiments, but that it have the full scope defined by the language of the following claims.

What we claimed is:

1. A method for cleaning exhaust of an internal combustion engine having a catalyst and a lambda probe disposed in an exhaust gas tract, the lambda probe being disposed upstream from the catalyst, the lambda probe outputting a $\lambda o$ substantially close to lambda=1, the method comprising the steps of:

determining a relationship between a downstream NOx concentration and a lambda value such that a lambda value substantially greater than 1 indicates a substantially greatly increased NOx concentration;

determining a relationship between a downstream $NH_3$ concentration and a lambda value such that a lambda value substantially less than 1 indicates a substantially greatly increased $NH_3$ concentration;

disposing an NOx measuring pickup having a cross-sensitivity to $NH_3$ downstream from the catalyst;

measuring a downstream NOx concentration with the pickup;

measuring a downstream $NH_3$ concentration with the pickup; and correcting $\lambda o$ based on a relationship between a lambda from the lambda probe and the downstream NOx concentration.

2. The method according to claim 1, further comprising the steps of:

disposing an NOx storing or reducing catalyst in the exhaust tract; and controlling an operation of the NOx catalyst with the pickup.

3. The method according to claim 1, further comprising the step of:

measuring a first output from the pickup which changes sign at substantially lambda=1.

4. The method according to claim 3, further comprising the step of:

dispersing a mixture of fuel and air to the internal combustion engine, a composition of the mixture chosen such that a second output of the pickup indicates a predetermined NOx concentration corresponding to $\lambda o$, and the sign of the first output from the pickup is evaluated to determine whether the second output is in a range corresponding to lambda<1 or a range corresponding to lambda>1.

5. The method according to claim 4, wherein the pickup further comprises an oxygen measuring cell.

6. The method according to claim 5, further comprising the step of:

adjusting a current in the oxygen measuring cell of the pickup, such that the oxygen concentration in the measuring cell is adjusted to a value corresponding to lambda=1.

7. A method for cleaning exhaust of an internal combustion engine having a catalyst and a lambda probe disposed in an exhaust gas tract, the lambda probe being disposed upstream from the catalyst, the lambda probe outputting a $\lambda o$ substantially close to a predetermined limit, the method comprising the steps of:

determining a relationship between a downstream NOx concentration and a lambda value such that a lambda value substantially greater than the predetermined limit indicates a substantially greatly increased NOx concentration;

determining a relationship between a downstream $NH_3$ concentration and a lambda value such that a lambda value substantially less than a predetermined limit indicates a substantially greatly increased $NH_3$ concentration;

disposing an NOx measuring pickup having a cross-sensitivity to $NH_3$ downstream from the catalyst;

measuring a downstream NOx concentration with the pickup;

measuring a downstream $NH_3$ concentration with the pickup; and correcting $\lambda o$ based on a relationship between a lambda from the lambda probe and the downstream NOx concentration.

8. The method according to claim 7, further comprising the steps of:

measuring a first output from the pickup which changes sign at lambda substantially equal to the predetermined limit; and dispersing a mixture of fuel and air to the internal combustion engine, a composition of the mixture chosen such that a second output of the pickup indicates a predetermined NOx concentration corresponding to $\lambda o$, and the sign of the first output from the pickup is evaluated to determine whether the second output is in a range corresponding to lambda substantially less than the predetermined limit or a range corresponding to lambda substantially greater than the predetermined limit.

9. The apparatus according to claim 8, further comprising:

an operation control apparatus, the operation control apparatus controlling the operation of the internal combustion engine such that an exhaust at the lambda probe is a predetermined value.

10. The apparatus according to claim 9, wherein the pickup delivers an output which changes sign at substantially lambda=1.

11. The apparatus according to claim 10, wherein the operation control apparatus is adapted to receive a signal from the pickup which corresponds to a sign change.

12. The apparatus according to claim 11, wherein the operation control apparatus is adapted to receive a signal from the pickup which corresponds to a lambda substantially greater than one and substantially less than one.

13. The apparatus according to claim 12, wherein the operation control apparatus controls the operation of the internal combustion engine, thereby effectively correcting $\lambda o$ based on a relationship between a lambda from the lambda probe and the downstream NOx concentration.

14. The apparatus according to claim 13, wherein the pickup includes a first measuring cell where a portion of the exhaust is introduced and an oxygen concentration is adjusted by means of an oxygen ion pumping current, the oxygen ion pumping current being one of the signals output by the pickup.

15. The apparatus according to claim 14, wherein the pickup includes a second measuring cell connected to the first measuring cell where a second oxygen concentration is adjusted, an NOx concentration being measured with a measuring electrode.

16. An apparatus for cleaning exhaust of an internal combustion engine, comprising:

an exhaust gas tract;

a catalyst disposed in the exhaust gas tract;

a lambda probe disposed in the exhaust gas tract upstream from the catalyst, the lambda probe outputting a $\lambda o$ substantially close to lambda=1;

an NOx measuring pickup having a cross-sensitivity to $NH_3$ disposed in the exhaust gas tract downstream from the catalyst, wherein a downstream NOx concentration measured by the pickup corresponds to a lambda value such that a lambda value substantially greater than 1 indicates a substantially greatly increased NOx concentration, and a downstream $NH_3$ concentration measured by the pickup corresponds to a lambda value such that a lambda value substantially less than 1 indicates a substantially greatly increased $NH_3$ concentration.

* * * * *